United States Patent
Guan et al.

(10) Patent No.: US 7,971,776 B2
(45) Date of Patent: Jul. 5, 2011

(54) ULTRASONIC INSTRUMENT AND METHOD FOR CONTROLLING ITS MULTIPLE PROBES

(75) Inventors: Zhiyong Guan, Shenzhen (CN);
Zhengpeng Fu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 388 days.

(21) Appl. No.: 12/269,671

(22) Filed: Nov. 12, 2008

(65) Prior Publication Data
US 2009/0121008 A1    May 14, 2009

(30) Foreign Application Priority Data

Nov. 12, 2007   (CN) .......................... 2007 1 0124528

(51) Int. Cl.
*G06F 17/00*   (2006.01)
(52) U.S. Cl. ....................................... 235/375; 235/439
(58) Field of Classification Search .................. 235/375, 235/439; 703/584
See application file for complete search history.

(56) References Cited

U.S. PATENT DOCUMENTS
2004/0171935 A1    9/2004   Van Creveld et al.

FOREIGN PATENT DOCUMENTS
| CN | 2717391 Y | 8/2005 |
| CN | 1672639 A | 9/2005 |
| EP | 1676530 A1 | 7/2006 |
| JP | 59197855 A | 11/1984 |
| WO | 9831285 A1 | 7/1998 |

*Primary Examiner* — Edwyn Labaze
(74) *Attorney, Agent, or Firm* — Kory D. Christensen; Stoel Rives LLP

(57) ABSTRACT

An ultrasonic instrument includes a socket and a front-end system, wherein the socket is provided with at least two probe model identification pins and a plurality of functional signal pins. The front-end system comprises a decoding module, a switch selection module, and a probe driving control module. The decoding module has its input terminals electrically connected to the probe model identification pins of the socket, and has its output terminal coupled to the control terminal of the switch selection module. The input terminals of the switch selection module are electrically connected to the functional signal pins of the socket respectively, and in response to a probe identification signal outputted from the decoding module to the control terminal, the switch selection module establishes connection between its input terminals and a group of output terminals corresponding to the probe identification signal. The probe driving control module is electrically connected to the output terminals of the switch selection module.

10 Claims, 6 Drawing Sheets

| No. | Signal Name | Definition |
|---|---|---|
| 1 | S0 | Ordinary one-dimensional probe ID reading signal 1 |
| 2 | S1 | Ordinary one-dimensional probe ID reading signal 2 |
| 3 | S2 | Ordinary one-dimensional probe ID reading signal 3 |
| 4 | S3 | Ordinary one-dimensional probe ID reading signal 4 |
| 5 | S4 | Ordinary one-dimensional probe ID reading signal 5 |
| 6 | S5 | Ordinary one-dimensional probe ID reading signal 6 |
| 7 | Probe_On1 | Probe type decoding signal 1 |
| 8 | Probe_On2 | Probe type decoding signal 2 |

| No. | Signal Name | Definition |
|---|---|---|
| 1 | S0 | Ordinary one-dimensional probe ID reading signal 1 |
| 2 | S1 | Ordinary one-dimensional probe ID reading signal 2 |
| 3 | S2 | Ordinary one-dimensional probe ID reading signal 3 |
| 4 | S3 | Ordinary one-dimensional probe ID reading signal 4 |
| 5 | S4 | Ordinary one-dimensional probe ID reading signal 5 |
| 6 | S5 | Ordinary one-dimensional probe ID reading signal 6 |
| 7 | Probe_On1 | Probe type decoding signal 1 |
| 8 | Probe_On2 | Probe type decoding signal 2 |

Fig. 1

| No. | Signal Name | Definition |
|---|---|---|
| 1 | D0 | Special probe control signal 1 |
| 2 | D1 | Special probe control signal 2 |
| 3 | D2 | Special probe control signal 3 |
| 4 | D3 | Special probe control signal 4 |
| 5 | D4 | Special probe control signal 5 |
| 6 | D5 | Special probe control signal 6 |
| 7 | Probe_On1 | Probe type decoding signal 1 |
| 8 | Probe_On2 | Probe type decoding signal 2 |

Fig. 2

ULTRASONIC INSTRUMENT AND METHOD FOR CONTROLLING ITS MULTIPLE PROBES

CROSS-REFERENCE TO RELATED APPLICATIONS

This application claims priority to Chinese Patent Application No. 200710124528.X, filed Nov. 12, 2007, for "Ultrasonic Instrument and Method for Controlling Its Multiple Probes," which is incorporated herein by reference in its entirety.

TECHNICAL FIELD

This disclosure relates to diagnostic ultrasound.

BRIEF SUMMARY

An ultrasonic instrument for identifying and controlling multiple probes and a method for controlling the probes are disclosed.

BRIEF DESCRIPTION OF THE DRAWINGS

FIG. 1 shows the definitions of interface signals of an ordinary probe;

FIG. 2 shows the definitions of interface signals of a special probe;

DETAILED DESCRIPTION

Figure 3:
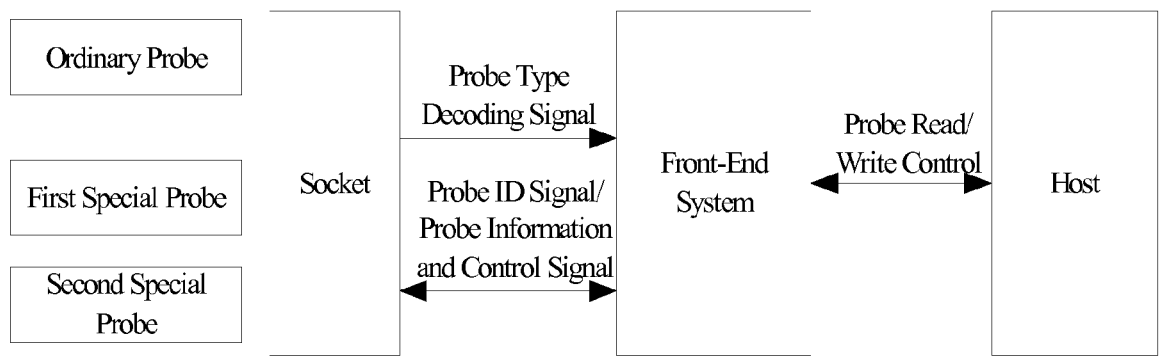
FIG. 3 is an overall block diagram of probe identification and control.

In an ultrasonic instrument, a front-end system is generally required to identify the model of an ultrasonic probe and communicate it to a host, which controls scan operations in accordance with the model of the ultrasonic probe. The process for plugging and unplugging the ultrasonic probe typically involves informing, by means of a probe in-situ signal, the host that the probe has been connected properly, reading the probe ID code by the host in a fixed manner (i.e., via a parallel interface or a serial interface) to identify the probe model, and controlling scan operations of the probe by the host in accordance with the probe model.

The present disclosure differentiates between "ordinary" and "special" probes for use in diagnostic ultrasound. Ordinary probes include standard circuits for processing echo signals and generating an ID code. By contrast, special probes include not only the standard circuits for processing echo signals and generating an ID code, but also include additional circuits, motors, and/or sensors. For example, a three-dimensional ("3D/4D") probe includes a motor and a position sensor; a transesophageal echocardiography ("TEE") probe includes a temperature sensor; a Biplane probe includes a high-voltage switching circuit, etc. Various other types of special probes are known to skilled artisans and are contemplated herein. Exemplary ordinary probes include the 3C5 and 7L4 probes manufactured by Shenzhen Mindray Bio-Medical Electronics, Co., Ltd. of Shenzhen, People's Republic of China. Examples of special probes include the P7-3 TEE TEE probe and the 4CD4 3D/4D probe manufactured by Shenzhen Mindray Bio-Medical Electronics, Co., Ltd.

The control pins of special probes, such as 3D/4D and TEE probes, are rather different from those of ordinary one-dimensional probes. Since different kinds of probes having the same number of array elements have the same number of signal pins, and the number of the control pins of ordinary probes is also the same, the same type of probe sockets may be used.

The interfaces of control pins for an ordinary one-dimensional probe are shown in FIG. 1. However, the definitions of, and thus the functions of, the control pins of special probes, such as 3D/4D probes and TEE probes, are different from those of the control pins of ordinary one-dimensional probes in that dedicated signals, such as probe temperature information return and motor driving signals, are included.

FIG. 2 shows the definitions of the interfaces of the control pins for special probes. The number of the pins of a probe socket mainly depends on the total number of signal pins and control pins of the probe. However, the number of the pins of ordinary probe sockets is limited. In prior systems, when the control pins of different kinds of special probes cannot be received at one common probe socket due to the limited number of the pins of the probe socket, the probe sockets for special probes and the probe sockets for ordinary one-dimensional probes have to be provided separately. At present, it is common practice to provide two types of sockets in an ultrasonic instrument, one only for a special probe, and the other only for an ordinary one-dimensional probe. This has a disadvantage of increased hardware cost and occupied space.

The present disclosure provides an ultrasonic instrument and a method for controlling its multiple probes, such that an ordinary probe and a special probe may share one socket, thereby reducing the number of sockets and saving space in the ultrasonic instrument.

According to one aspect of the disclosure, there is provided an ultrasonic instrument that includes a socket and a front-end system, wherein the socket is provided with at least two probe model identification pins and a plurality of functional signal pins; and the front-end system comprises a decoding module, a switch selection module, and a probe driving control module. In one configuration, the decoding module has its input terminals electrically connected to the probe model identification pins of the socket for inputting the level combination code of the probe model identification pins, and has its output terminal coupled to a control terminal of the switch selection module for outputting a corresponding probe identification signal to the switch selection module. The input terminals of the switch selection module may be electrically connected to the functional signal pins of the socket respectively, and the switch selection module may establish connection between its input terminals and a group of output terminals corresponding to the probe identification signal, in response to the probe identification signal outputted from the decoding module. The probe driving control module may be electrically connected to the output terminals of the switch selection module.

According to another aspect of the disclosure, an ultrasonic instrument includes at least one ordinary probe, at least one special probe, a socket that is shared by the ordinary probe and the special probe, and a front-end system. In one embodiment, both the ordinary probe and the special probe are provided with at least two probe model identification probe tips and a plurality of functional signal probe tips. The socket is provided with at least two probe model identification pins for respectively receiving the probe model identification probe tips and with a plurality of functional signal pins for respectively receiving the functional signal probe tips.

In one embodiment, the front-end system comprises a decoding module, a switch selection module, and a probe driving control module. The decoding module has its input terminals electrically connected to the probe model identification pins of the socket for inputting the level combination code of the probe model identification pins, and has its output terminal coupled to a control terminal of the switch selection module for outputting a corresponding probe identification signal to the switch selection module. The input terminals of the switch selection module may be electrically connected to the functional signal pins of the socket respectively, and the switch selection module may establish connection between its input terminals and a group of output terminals corresponding to the probe identification signal, in response to the probe identification signal outputted by the decoding module. The probe driving control module may be electrically connected to the output terminals of the switch selection module.

According to still another aspect of the present disclosure, an ultrasonic instrument includes a socket, a front-end system, and a host, wherein the socket is provided with at least two probe model identification pins and a plurality of functional signal pins. In one configuration, the front-end system comprises a decoding module, a switch selection module, and a probe driving control module. The decoding module may have its input terminals electrically connected to the probe model identification pins of the socket for inputting the level combination code of the probe model identification pins, and may have its output terminal coupled to a control terminal of the switch selection module for outputting a corresponding probe identification signal to the switch selection module. In one embodiment, input terminals of the switch selection module are electrically connected to the functional signal pins of the socket, respectively, and the switch selection module establishes connection between its input terminals and a group of output terminals corresponding to the probe identification signal, in response to the probe identification signal outputted by the decoding module. The probe driving control module may be electrically connected between the output terminals of the switch selection module and the host, for transmission of data or commands between the switch selection module and the host.

According to yet another aspect of present disclosure, there is also provided a method for controlling multiple probes of an ultrasonic instrument, including the following steps:

A. providing a socket to be shared by ordinary probes and special probes, the socket being provided with at least two probe model identification pins and a plurality of functional signal pins;

B. upon plugging a probe into the socket, outputting a corresponding decoding result based on a detected level combination code of the at least two probe model identification pins of the socket;

C. establishing a connection between a probe driving circuit corresponding to the decoding result and the current probe;

D. obtaining an identification code of the current probe, and

E. selecting a scan control procedure corresponding to the current probe to perform scan control for the probe.

In comparison with prior approaches, the disclosed apparatus and method achieves the following effects:

1. An ordinary one-dimensional probe socket can be adopted not only to control, identify, and receive a special probe, but also to receive an ordinary one-dimensional probe, such that there is no need to provide multiple sockets. This results in greater ease of use, while reducing the space occupied by sockets.

2. The identification method is simplified by identifying a probe type by means of hardware control instead of software control.

3. There is no need for additional control signals. That is, an ordinary one-dimensional probe socket may receive a special probe, thereby reducing the number of control pins of a probe and ensuring forward compatibility of a product.

Referring now to FIG. 3, there is shown a block diagram of an overall system for probe identification and control. The system includes a probe, a socket, a front-end control system, and a host, as well as standard components not specifically identified. The socket, the front-end control system, and the host may be electrically connected in a sequential fashion.

In one embodiment, the probe tips of a probe include at least two probe model identification probe tips and a plurality of functional signal probe tips, while the socket is accordingly provided with at least two probe model identification pins and a plurality of functional signal pins. The probe is plugged into the socket in order to electrically connect to the front-end control system.

The probe model identification probe tips may include two probe in-situ signal probe tips, Probe_On1 and Probe_On2, and the probe model identification pins of the socket include two probe in-situ signal pins. The level combination from the two probe in-situ signal probe tips of the ordinary probe and special probe results in four kinds of codes.

In order to be compatible with existing technologies, for an ordinary probe that employs only one bit probe in-situ signal (Probe_On1), another bit probe in-situ signal (Probe_On2) of the probe in-situ signals may be set to a signal ground defined by the original probe. In order to generate a level code corresponding to the model of the probe when it is plugged into the socket, it is required to design in-situ signal circuits for the socket and the probe.

Figure 4:
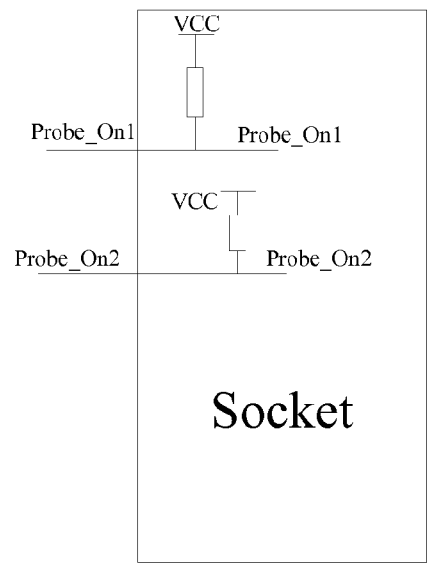
FIG. 4 is a circuit diagram of probe model identification pins within a socket.
Figure 5:
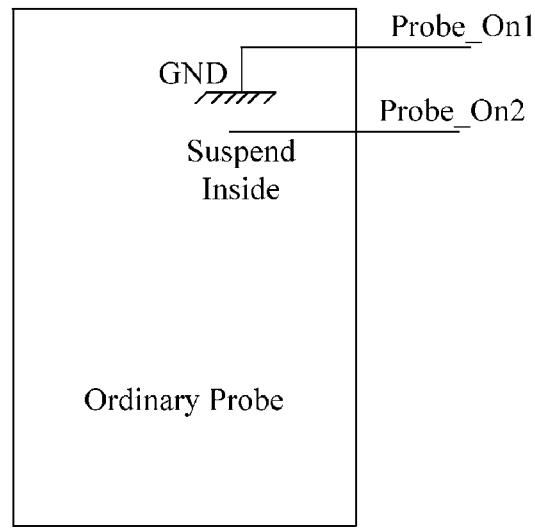
FIG. 5 is a circuit diagram of probe model identification probe tips within an ordinary probe.
Figure 6:
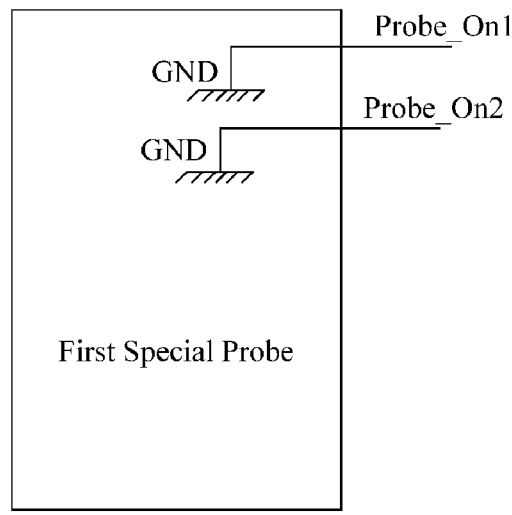
FIG. 6 is a circuit diagram of probe model identification probe tips within a first special probe.
Figure 7:
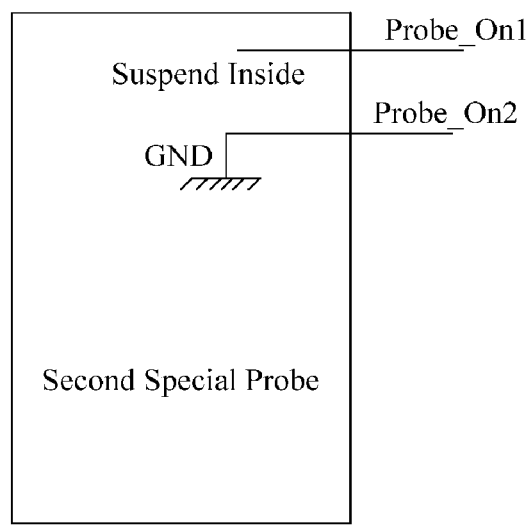
FIG. 7 is a circuit diagram of probe model identification probe tips within a second special probe.

FIGS. 4-7 show embodiments for in-situ signal circuits of a socket, of an ordinary probe, and of first and second special probes. In FIG. 4, each of Probe_On1 and Probe_On2 is connected to a power supply VCC via a pull-up resistor. For the ordinary probe as shown in FIG. 5, Probe-On1 is suspended and Probe_On2 is grounded. For the first special probe as shown in FIG. 6, Probe_On1 is grounded and Probe_On2 is suspended. For the second special probe, as shown in FIG. 7, both Probe_On1 and Probe_On2 are grounded. Thus, the combination (1, 1) of (Probe_On1, Probe_On2) may represent no probe, the combination (0, 1) may represent the ordinary probe, the combination (0, 0) may represent the first special probe type, and the combination (1, 0) may represent the second special probe type, thereby maintaining forward compatibility of a product.

Probes may be of numerous types, but may be divided into ordinary one-dimensional probes and special probes in accordance with the difference between interface definitions. There are many types of special probes, such as 3D/4D probes and TEE probes. Moreover, there are many specific models for each type of probes, and different scan control procedures are used for different specific models. The specific model of a probe may be identified from the ID code (identification code) of the probe.

The front-end control system may be used to identify the probe in-situ signal to make a decision, read the ID code of the probe under control of the host, and send it to the host via a uniform interface.

The host performs scan control for the probe through the front-end control system based on the ID code of the probe.

Figure 8:
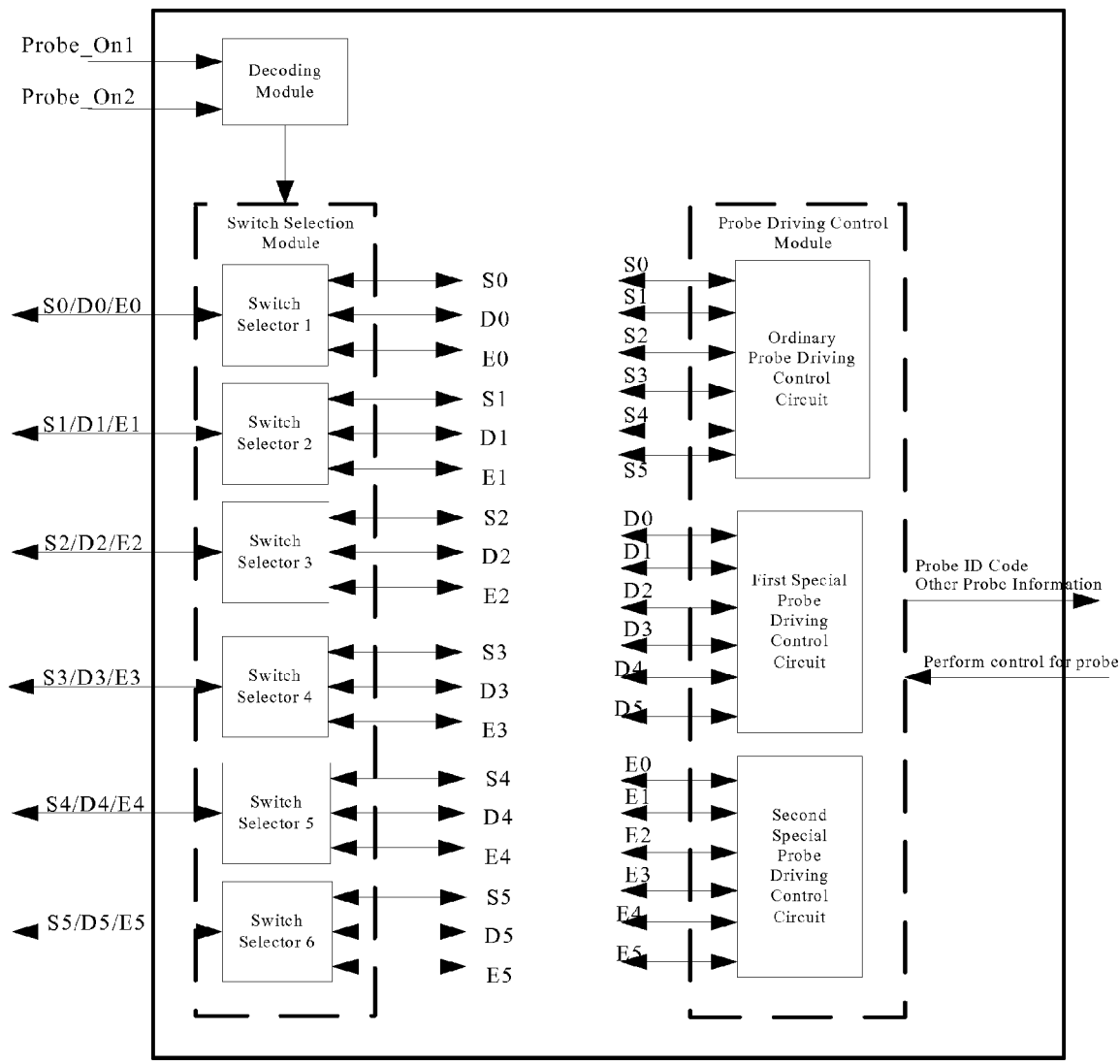
FIG. 8 is a block diagram of the internal structure of a front-end system according to an embodiment of the present disclosure.
Figure 9:
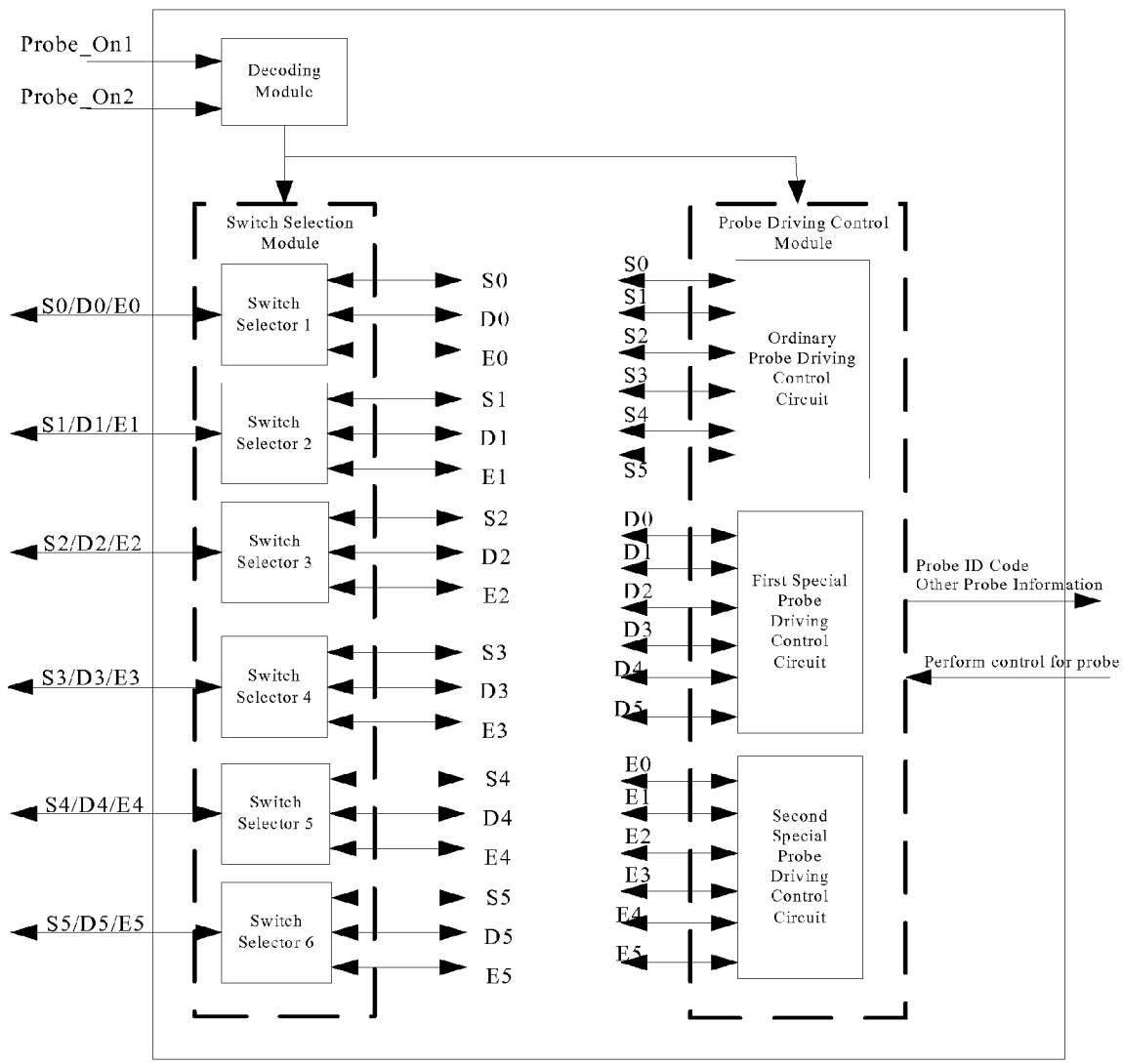
FIG. 9 is a block diagram of the internal structure of a front-end system according to another embodiment of the present disclosure.

In one embodiment, the front-end system comprises a decoding module, a switch selection module, and a probe driving control module, among other things. FIG. 8 is a block diagram of the front-end system.

The decoding module may be electrically connected to the probe model identification pins of the socket, i.e., to the probe in-situ signal probe tips Probe_On1 and Probe_On2, for inputting a level combination code of the probe model identification pins and for outputting a corresponding probe identification signal to the control terminal of the switch selection module. The input terminals of the switch selection module are electrically connected to the functional signal pins of the socket respectively, i.e., to the functional signal probe tips of the probe. In response to the probe identification signal received at the control terminal, the switch selection module establishes connection between its input terminals and a group of output terminals corresponding to the probe identification signal. The probe driving control module is connected between the output terminals of the switch selection module and the host.

Each switch in the switch selection module may be implemented in various devices, such as a relay, an analog switch, multi-way switch, and the like.

The probe driving control module may include an ordinary probe driving circuit, a first special probe driving circuit and a second special probe driving circuit.

The decoding module may be used to perform decoding and make decisions with respect to the level combination coding states of the probe in-situ signals Probe_On1 and Probe_On2, and distinguish the type of the probe currently connected. In one embodiment, four states may be decoded from the two-bit probe in-situ signal, and may represent four instances of "no probe", "ordinary probe", "first special probe type," and "second special probe type".

In the case where there are four states to be decoded, the switch selection module may divide the control signal that connects the front-end with the probe into three signals via the switch selection circuit. Which one of these three signals should be specifically outputted is controlled by the output from the decoding module. The number of the switches in the switch selection module is the same as the number of the functional signal probe tips of the probe. For example, when the output from the decoding module corresponds to the instance of "ordinary probe," each switch in the switch selection module respectively selects S0, S1, S2, S3, S4 and S5 to output, so that the ordinary probe driving control circuit of the probe driving control module is electrically connected to the current probe. Similarly, if the output from the decoding module corresponds to the instance of "first special probe," the switch selection module will establish electrical connection between the first special probe driving control circuit in the probe driving control module and the current probe.

When the probe is connected to the host, the decoding module outputs a probe type signal obtained by decoding, and the probe driving control module then operates in accordance with the probe type signal in various ways. One way is to automatically read the ID code of the probe, and upload the ID code to the host, which distinguishes the specific probe model upon receipt of the ID code, and performs scan control operation for the probe via corresponding probe driving control circuit in accordance with the control mode for the specific probe model. Another way is to simply inform the host of probe in-situ information and probe type information, and the host reads the ID code of the probe in a manner corresponding to the probe type, and then performs scan control operation for the probe via a corresponding probe driving control circuit in accordance with the control mode for the specific probe model.

In another embodiment, the output from the decoding module also is used to control the probe driving control module, and, in particular, is connected to one of the enable terminals of various probe driving control circuits in the probe driving control module to enable a corresponding probe driving control circuit and disable the others, thereby reducing power consumption.

In the above embodiments, the front-end system communicates data and/or commands with the host in a wired or wireless manner. However, the host may be omitted, the functions of which may be integrated into the front-end system.

Those skilled in the art will appreciate that the decoding of a probe model may be implemented in other combinations, and the number of the probe model identification pins on a socket and the number of the probe model identification probe tips of a probe may also vary with the number of the probes that share the socket. For example, if the number of the probe model identification pins on a socket is three, then seven types of probes may be identified by the decoding module.

Although the invention has been described in more details above with reference to specific embodiments thereof, it is not intended that the specific embodiments of the present disclosure be limited to this description. Those skilled in the art to which the present disclosure belongs will appreciate that without departing from the inventive concept of the present disclosure, numerous simple derivatives and substitutions may also be made, which should be considered to be within the scope of protection of the present invention.

What is claimed is:

1. An ultrasonic instrument, comprising:
a socket; and
a front-end system,
wherein the socket is provided with at least two probe model identification pins and a plurality of functional signal pins;
wherein the front-end system comprises a decoding module, a switch selection module, and a probe driving control module;
wherein the decoding module has its input terminals electrically connected to the probe model identification pins of the socket, and has its output terminal coupled to a control terminal of the switch selection module;
wherein input terminals of the switch selection module are electrically connected to the functional signal pins of the socket, respectively, and in response to a probe identification signal outputted from the decoding module to the control terminal, the switch selection module establishes connection between its input terminals and a group of output terminals corresponding to the probe identification signal; and
wherein the probe driving control module is electrically connected to the output terminals of the switch selection module.

2. The ultrasonic instrument according to claim 1, wherein the output terminal of the decoding module is also coupled to the probe driving control module.

3. The ultrasonic instrument according to claim 1, wherein the probe driving control module comprises an ordinary probe driving circuit, a first special probe driving circuit, and a second special probe driving circuit.

4. The ultrasonic instrument according to claim 1, wherein the switch selection module is one of a relay or a multi-way selecting switch.

5. An ultrasonic instrument, comprising:
   at least one ordinary probe;
   at least one special probe;
   a socket that is shared by the ordinary probe and the special probe; and
   a front-end system,
   wherein both the ordinary probe and the special probe are provided with at least two probe model identification probe tips and a plurality of functional signal probe tips, and the socket is provided with at least two probe model identification pins for respectively receiving the probe model identification probe tips and with a plurality of functional signal pins for respectively receiving the functional signal probe tips;
   wherein the front-end system comprises a decoding module, a switch selection module, and a probe driving control module;
   wherein the decoding module has its input terminals electrically connected to the probe model identification pins of the socket, and has its output terminal coupled to a control terminal of the switch selection module;
   wherein input terminals of the switch selection module are electrically connected to the functional signal pins of the socket respectively, and in response to a probe identification signal outputted from the decoding module to the control terminal, the switch selection module establishes connection between its input terminals and a group of output terminals corresponding to the probe identification signal; and
   wherein the probe driving control module is electrically connected to the output terminals of the switch selection module.

6. The ultrasonic instrument according to claim 5, wherein the probe model identification probe tips of the ordinary probe and the special probe include two probe in-situ signal probe tips, the probe model identification pins of the socket include two probe in-situ signal pins, and level combination of two probe in-situ signal probe tips for the ordinary probe and the special probe is able to represent four kinds of codes.

7. An ultrasonic instrument, comprising:
   a socket;
   a front-end system; and
   a host,
   wherein the socket is provided with at least two probe model identification pins and a plurality of functional signal pins;
   wherein the front-end system comprises a decoding module, a switch selection module, and a probe driving control module;
   wherein the decoding module has its input terminals electrically connected to the probe model identification pins of the socket, and has its output terminal coupled to a control terminal of the switch selection module;
   wherein input terminals of the switch selection module are electrically connected to the functional signal pins of the socket respectively, and in response to a probe identification signal outputted from the decoding module to the control terminal, the switch selection module establishes connection between its input terminals and a group of output terminals corresponding to the probe identification signal; and
   wherein the probe driving control module is electrically connected between the output terminals of the switch selection module and the host, for transmission of data or commands between the switch selection module and the host.

8. A method for controlling multiple probes of an ultrasonic instrument, comprising the steps of:
   A. providing a socket to be shared by ordinary probes and special probes, the socket being provided with at least two probe model identification pins and a plurality of functional signal pins;
   B. upon plugging a probe into the socket, outputting a corresponding decoding result based on a detected level combination code of the at least two probe model identification pins of the socket;
   C. establishing connection between a probe driving circuit corresponding to the decoding result and the current probe; and
   D. obtaining an identification code of the current probe, and selecting a scan control procedure corresponding to the current probe to perform scan control for the current probe.

9. The method according to claim 8, wherein the step D comprises:
   D11. automatically obtaining the identification code of the current probe;
   D12. uploading the identification code of the current probe to the host;
   D13. distinguishing a specific probe model by the host based on the received identification code of the current probe; and
   D14. performing scan control for the probe by the host via the probe driving circuit in accordance with a control mode for the specific probe model.

10. The method according to claim 8, wherein the probe model identification pins of the socket include two probe in-situ signal pins, the probe type is identified by decoding level combination code of the two probe in-situ signal pins in the step B, and the step D comprises:
   D21. uploading probe in-situ information and probe type information to the host;
   D22. reading the identification code of the probe by the host in a manner corresponding to the probe type information; and
   D23. performing scan control for the probe by the host via the probe driving circuit in accordance with a control mode for the specific probe model.

* * * * *